(12) United States Patent
Cise et al.

(10) Patent No.: US 6,632,091 B1
(45) Date of Patent: Oct. 14, 2003

(54) ORAL CARE SYSTEM

(75) Inventors: David Cise, Sandy; Gene Stewart, Midvale; Warren Grant, Lehi; Sydnee McMillan, Sandy, all of UT (US)

(73) Assignee: Ballard Medical Products, Draper, UT (US)

( * ) Notice: Subject to any disclaimer, the term of this patent is extended or adjusted under 35 U.S.C. 154(b) by 0 days.

(21) Appl. No.: 09/351,015

(22) Filed: Jul. 12, 1999

Related U.S. Application Data

(63) Continuation of application No. 08/851,928, filed on May 6, 1997, now Pat. No. 6,129,547.

(51) Int. Cl.$^7$ ................................................ A61C 1/16
(52) U.S. Cl. ........................................ 433/116; 433/87
(58) Field of Search ............................ 433/80, 82, 91, 433/93–96, 215, 88, 229, 87, 116; 604/902, 275, 35, 36; 601/162, 165

(56) References Cited

U.S. PATENT DOCUMENTS

| | | | |
|---|---|---|---|
| 2,769,193 A | | 11/1956 | Jackson |
| 2,813,529 A | * | 11/1957 | Ikse ............................. 433/80 |
| 3,324,855 A | | 6/1967 | Heimlich |
| 3,618,596 A | | 11/1971 | Miller |
| 3,645,497 A | | 2/1972 | Nyboer |
| 3,745,655 A | * | 7/1973 | Malmin ......................... 433/80 |
| 3,943,592 A | | 3/1976 | Bhaskar et al. |
| 4,115,893 A | | 9/1978 | Nakata et al. |
| 4,215,746 A | | 8/1980 | Hallden et al. |
| 4,386,448 A | | 6/1983 | Kohn |
| 4,397,640 A | | 8/1983 | Haug et al. |
| 4,428,929 A | | 1/1984 | Wicheta et al. |
| 4,451,257 A | | 5/1984 | Atchley |
| 4,487,600 A | | 12/1984 | Brownlie et al. |
| 4,498,209 A | | 2/1985 | Weiss |
| 4,538,631 A | | 9/1985 | Prince |

(List continued on next page.)

FOREIGN PATENT DOCUMENTS

| | | |
|---|---|---|
| DE | 2728672 | 1/1979 |
| DE | 3327129 | 2/1985 |
| FR | 2569343 | 2/1986 |
| FR | 2734695 | 12/1996 |
| GB | 2067069 | 7/1981 |
| GB | 2223977 | 4/1990 |
| JP | 52087245 | 7/1977 |
| JP | 3188848 | 8/1991 |
| JP | 8112143 | 5/1996 |
| JP | 8182538 | 7/1996 |
| JP | 8275961 | 10/1996 |
| RO | 66256 | 5/1982 |
| RU | 2041673 | 8/1995 |
| SU | 1346125 | 10/1987 |
| SU | 1475579 | 4/1989 |
| SU | 1734676 | 5/1992 |

Primary Examiner—Nicholas D. Lucchesi
(74) Attorney, Agent, or Firm—Dority & Manning, P.A.

(57) ABSTRACT

An oral care system includes a universal handle which is configured to hold any of a plurality of oral hygiene instruments, and a lavage source to apply lavage solution through the oral hygiene instruments to facilitate complete cleaning of a patient's mouth. Preferably, the universal handle and lavage source are configured to be held in the user's hand with both suction and lavage being controlled manually. The orally hygiene instruments attachable to the universal handle typically include a lavage toothbrush, at least one catheter and at least one swab, to thereby enable cleaning of the teeth, gums, soft tissue and crevices therebetween.

29 Claims, 8 Drawing Sheets

U.S. PATENT DOCUMENTS

| | | |
|---|---|---|
| 4,672,953 A | 6/1987 | DiVito |
| 4,680,026 A | 7/1987 | Weightman et al. |
| 4,738,001 A | 4/1988 | Shipp |
| 4,822,278 A | 4/1989 | Oliva et al. |
| 4,831,676 A | 5/1989 | Denmark |
| 4,861,266 A | 8/1989 | Ashiku |
| 5,009,881 A | 4/1991 | Hill et al. |
| 5,024,615 A | 6/1991 | Büchel |
| 5,033,154 A | 7/1991 | Marchand et al. |
| 5,039,515 A | 8/1991 | Korf |
| 5,048,143 A | 9/1991 | Carroll |
| 5,054,154 A | 10/1991 | Schiffer et al. |
| 5,057,306 A | 10/1991 | Hill et al. |
| 5,057,307 A | 10/1991 | Hill et al. |
| 5,076,787 A | 12/1991 | Overmyer |
| 5,078,732 A | 1/1992 | Ceniceros |
| 5,094,616 A | 3/1992 | Levenson |
| 5,114,342 A | 5/1992 | Young et al. |
| 5,123,840 A | 6/1992 | Nates |
| 5,138,737 A | 8/1992 | Thomas |
| 5,145,367 A | 9/1992 | Kasten |
| 5,145,368 A | 9/1992 | Tomic |
| 5,151,094 A | 9/1992 | Hanifl |
| 5,291,878 A | 3/1994 | Lombardo et al. |
| 5,295,830 A | 3/1994 | Shen et al. |
| 5,458,563 A | 10/1995 | Stewart |
| 5,463,792 A | 11/1995 | Hogan et al. |
| 5,511,273 A | 4/1996 | Carroll |
| 5,571,140 A | 11/1996 | Gura-Emerling |
| 5,617,884 A | 4/1997 | Allison |
| 5,623,739 A | 4/1997 | Thompson |
| 5,634,791 A * | 6/1997 | Matsuura et al. ............. 433/87 |
| 5,636,405 A | 6/1997 | Stone et al. |
| 5,711,759 A | 1/1998 | Smith et al. |
| 5,729,859 A | 3/1998 | Guffin, III |

* cited by examiner

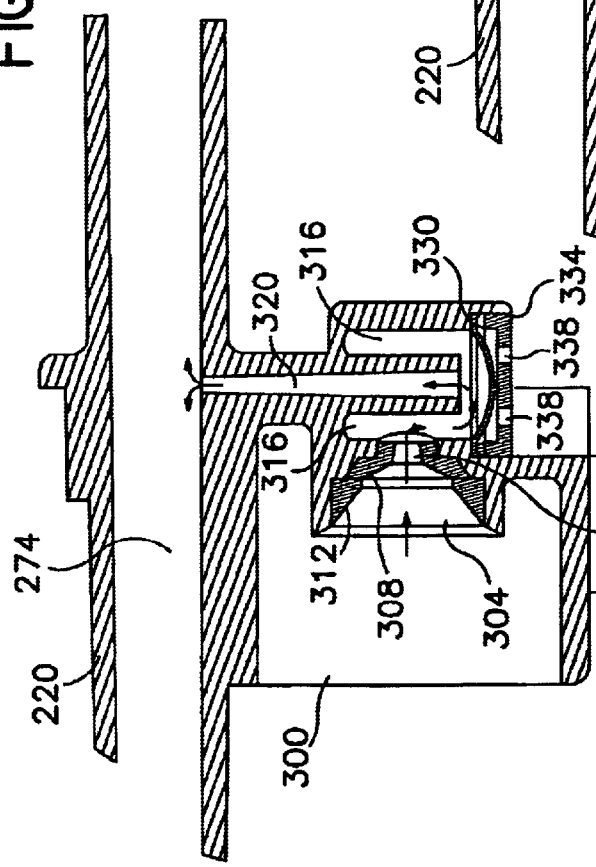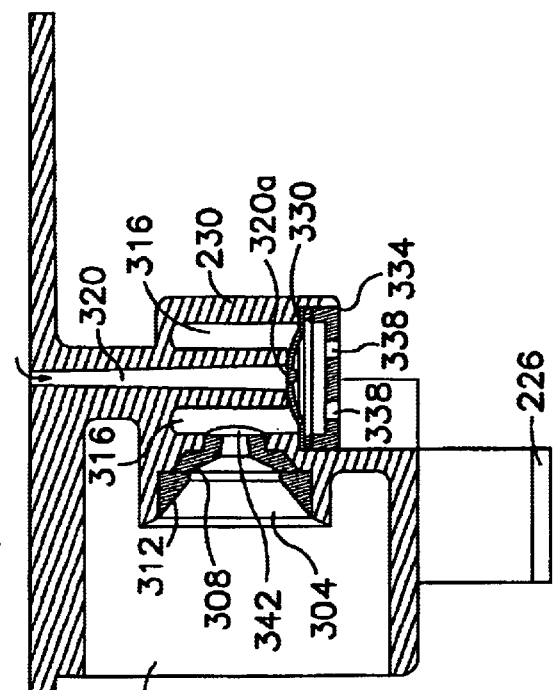

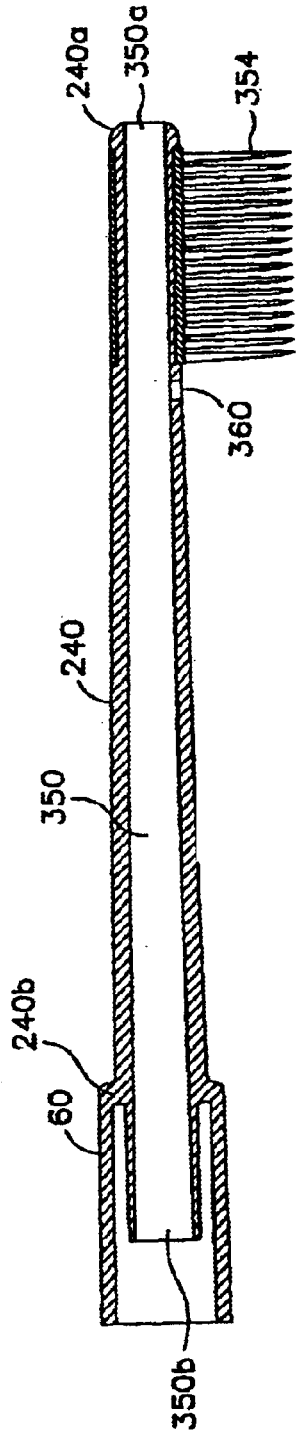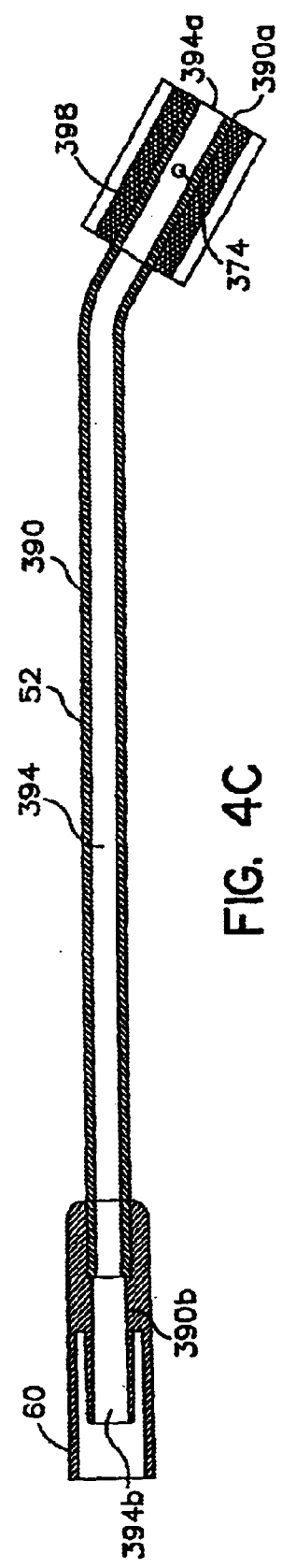

ORAL CARE SYSTEM

The present application is a continuation application of U.S. Ser. No. 08/851,928 filed on May 6, 1997, now U.S. Pat. No. 6,129,547 entitled "Oral Care System" and assigned to the same assignee of the present application.

BACKGROUND OF THE INVENTION

1. Field of the Invention

The present invention relates to an oral care system for cleaning the mouth of a patient having a temporary or permanent disability interfering with the patient's ability to practice oral hygiene. More particularly, the present invention relates to a system wherein a plurality of instruments are attachable to a common suction/lavage handle to facilitate cleaning the mouth of a bedridden or otherwise incapacitated patient who cannot regularly practice oral hygiene.

2. State of the Art

There are many situations in which an individual is temporarily or permanently unable to practice oral hygiene in a convenient manner. One particular problem is presented by critical care patients in hospitals, as well as those in hospitals and nursing homes who require respirators to breath. Not only can the patient typically not walk or otherwise move to a restroom, the patient is often unable to hold the tooth brush and other oral hygiene instruments which are commonly used to keep one's mouth clean.

Because of these problems, the oral hygiene of many patients must be conducted by nurses or nurse's aids. The oral hygiene for each such patient must be worked in to an already hectic routine. Therefore, it is common for oral hygiene to be omitted on any given day, and it is not uncommon for a patient to go several days without proper oral hygiene.

While devices to provide such oral hygiene have been suggested, each has disadvantages which limit its use on a broad scale. For example, U.S. Pat. No. 5,463,792, shows an aspirating toothbrush. The toothbrush has two passages formed therein. A first channel connects a lavage passage with an opening adjacent the bristles of the toothbrush. A second channel connects a plurality of holes disposed on the opposing side of the toothbrush opposite the bristles with a suction source. In use, the bristles are placed against the patients teeth or tongue and water or some other solution is injected into the patients mouth. The water or solution is then extracted through the holes on the opposite side of the toothbrush.

One problem with the toothbrush is that the position of the suction holes tends to bring them in contact with the soft tissue lining the mouth. If the tissue covers the holes, no suction relief is provided and the toothbrush becomes stuck to the side of the patient's mouth. If the suction is sufficient, the tissue can be damaged as the toothbrush is pulled away.

Another problem with the use of a suction toothbrush is that it provides only one tool for cleaning the mouth. Depending on the dental hygiene concern, several other devices may be desired to promote thorough and efficient cleaning. For example, a patient may be able to eat semisolid foods, but lack the motor coordination to brush his or her own teeth. To clean small pieces of food from between the cheek and gum, a long, thin catheter like instrument would be preferred. Using the toothbrush of the above referenced patent, however, would be more difficult, and would risk the toothbrush suctionally attaching to the wall of the patient's mouth.

U.S. Pat. No. 4,672,953 discloses an alternate embodiment of the toothbrush idea. The device avoids a substantial portion of the suction concern by placing the suction port between the bristles at the head of the toothbrush. In such a position, the suction opening would rarely come into direct contact with the soft tissue in the patient's mouth. Unfortunately, the configuration of the device makes it very difficult to use to clean between the cheek and gum, and in other small crevices in the mouth in which small particles of food can become trapped and cause irritation.

U.S. Pat. No. 5,114,342 discloses yet another device for withdrawing saliva from the mouth. While the device provides some control over saliva withdrawal, it does not provide lavage for cleaning or bristles for loosening plaque from the patient's teeth. Additionally, the head of the device is fairly large, limiting the use of the device for cleaning between the cheek and gum.

Still another attempt to facilitate dental hygiene for bedridden patients is shown in U.S. Pat. No. 5,458,563. The device includes a toothbrush having two channels, one for lavage and one for suction. In recognition of the necessity of only using a toothbrush for a single patient, the toothbrush is detachable from a suction hose. Unfortunately, the device suffers from the same disadvantages discussed above.

In addition to the need to clean teeth and between the cheek and gums, many patients will need to have their entire mouths washed to remove dried saliva, food particles and the like, as well as the removal of bacterial growth. While the devices discussed above will provide some moisturization, they do not provide the user with a tool to clean such materials from the soft tissue within the mouth.

Yet another problem which is not resolved by the prior art is the need to maintain the suction/lavage source free from contamination. If replaceable toothbrushes and the like are used with a common suction/lavage source, as suggested by U.S. Pat. No. 5,458,563, some mechanism must be provided to ensure that bacteria, viruses, etc., are not reintroduced to the patient with each subsequent use of the suction/lavage source.

Thus, there is a need for an improved oral care system. Such a system would enable the user to thoroughly clean each portion of a patient's mouth, and would enable lavage and suction without causing damage to the soft tissue thereof. Additionally, such a device should be relatively inexpensive to manufacture so that a single oral care system may have a single patient use, thereby preventing cross contamination between patients. Furthermore, such a device should be configured to maintain any contamination within the system such that the nurse or nursers aid using the system need not contact contaminated bodily fluids of the patient.

SUMMARY OF THE INVENTION

Thus, it is an object of the present invention to provide an improved oral care system which can be used to more completely and efficiently clean the mouths of bedridden patients.

It is another object of the present invention to provide such an oral care system wherein a plurality of different oral hygiene instruments are usable with a universal handle to decrease the need for equipment and decrease cost of a suction/lavage device to which the dental hygiene instruments may be used.

It is yet another object of the present invention to provide such an oral care system wherein the system is configured to minimize "external" or "surface" contamination of the universal handle, thereby keeping bodily fluids of the patient away from the health care professional using the device to clean the patient's mouth.

It is yet another object of the present invention to provide an oral care system utilizing suction and lavage, wherein the suction and lavage are supplied through a single fluid flow port to simplify construction of the oral hygiene instruments which are connectable to the universal handle.

It is still yet another object of the present invention to provide such a oral care system, wherein a valve configuration is provided which automatically prevents withdrawal of lavage liquid from the lavage liquid source by means of the suction, but which may be overcome at the option of the user and which does not otherwise interfere with the flow of the lavage liquid.

The above and other objects of the invention are realized in specific illustrated embodiments of an oral care system including a universal handle which is configured for attachment to a suction mechanism, a lavage mechanism and a plurality of dental hygiene instruments usable to clean the mouth of a patient. The oral care system also includes a plurality of dental hygiene instruments, typically including a toothbrush, swabs and catheters which can be used to supply water to and withdraw liquids from the patient's mouth. The handle has a universal adapter to enable each of the dental hygiene instruments to be attached to a port thereon, thereby enabling a single handle to be used for all of the patient's oral hygiene needs.

In accordance with one aspect of the present invention, the handle and dental hygiene instruments are configured to provide both lavage and suction through a common fluid flow passage, thereby making the oral care system easy to use, while simultaneously decreasing the complexity and cost of the respective parts. A special valve configuration may be used on the handle to passively terminate lavage flow to prevent the suction from draining the lavage supply. The valve configuration, however, enables the user to overcome the termination of lavage flow to flush the handle while suction is provided.

In accordance with another aspect of the present invention, the universal adapter which is used to enable attachment of each of the oral hygiene instruments is configured to engage the hygiene instruments in such a manner that both internal and external contamination of the end of handle is kept to a minimum. Thus, the risk that health care professionals will come into contact with bodily fluids of the patient when contacting the handle is reduced.

Preferably, both the suction and the lavage are controllable from the universal handle and by use of a single hand. Additionally, it is highly desirable that both suction and lavage be controlled manually, both to keep the universal handle simple, and to improve control of the suction and lavage. Thus, a nurse or nurse's aid is able to clean the patient's entire mouth with only one hand; enabling the other hand to be used to hold respiratory equipment and the like.

BRIEF DESCRIPTION OF THE DRAWINGS

The above and other objects, features and advantages of the invention will become apparent from a consideration of the following detailed description presented in connection with the accompanying drawings in which:

FIG. 3B shows a close-up, assembled view of the valve configuration of FIG. 3A with the valve in a first, open position to enable the flow of a lavage liquid through the lavage control housing;

FIG. 3C shows a close-up, assembled view of the valve configuration shown in FIGS. 3A and 3B with the valve in a second, closed position to prevent flow of a lavage liquid through the lavage control housing;

FIG. 4A shows a cross-sectional view of the toothbrush of FIG. 2;

FIG. 4C shows a cross-sectional view of the suction swab shown in FIG. 2.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
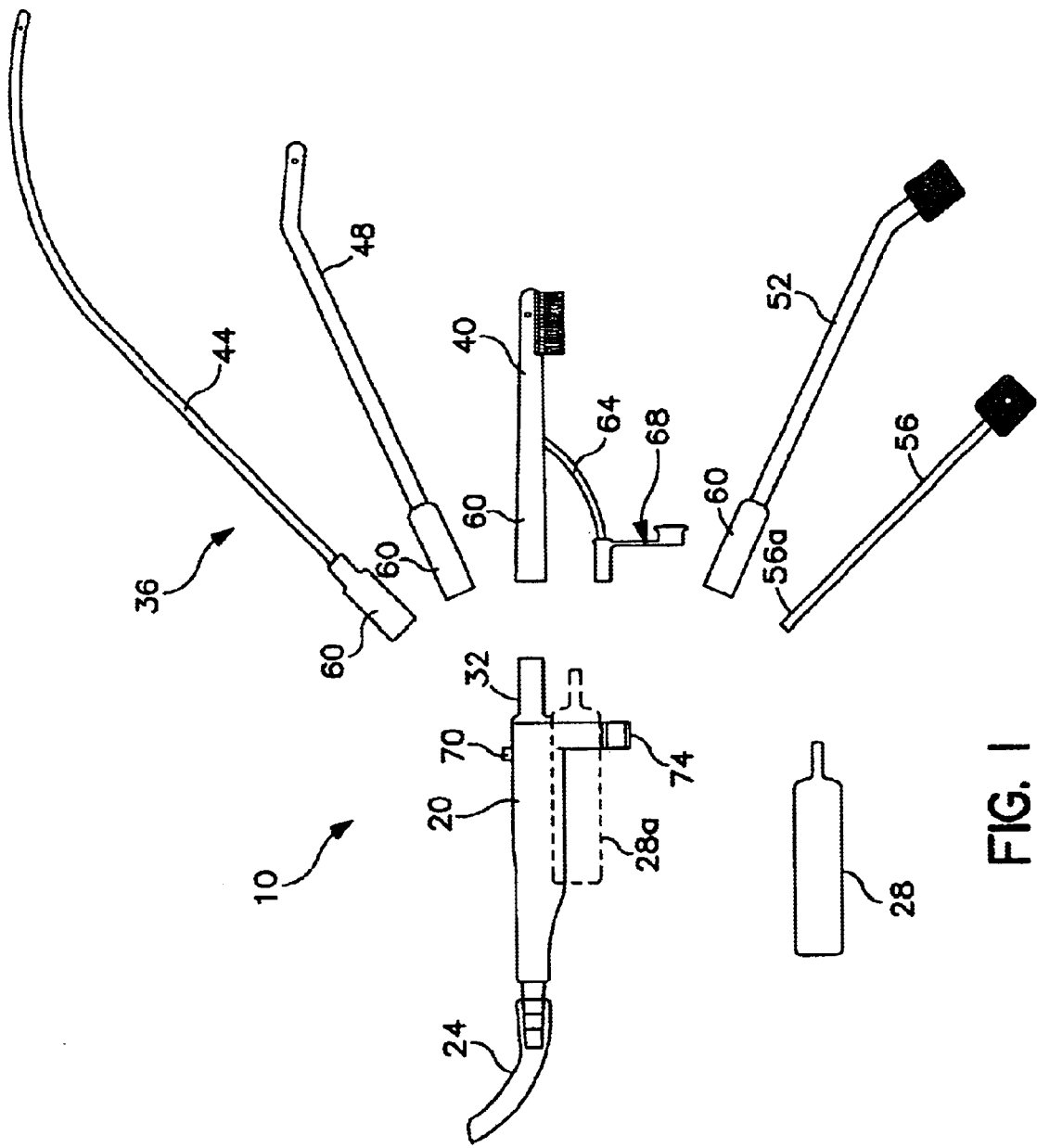
FIG. 1 shows one embodiment of a universal handle, a lavage source, and a plurality of oral hygiene instruments in accordance with the principles of the present invention.

Referring to FIG. 1, there is shown the various components of an oral care system, generally indicated at 10, made in accordance with the principles of the present invention. The oral care system 10 includes a universal handle 20 which is configured for attachment to a suction tube 24, and a lavage supply source 28 in the form of a disposable plastic vial. The universal handle 20 also includes an adapter end 32 which is configured to enable attachment of a plurality of different oral hygiene instruments, generally indicated at 36, to the universal handle.

Typically, the oral hygiene instruments 36, which are attachable to the universal handle 20, will include a toothbrush 40, at least one catheter (either a oropharangeal catheter 44 or a yankauer catheter 48), and at least one swab (either a suction swab 52 or a denta swab 56). Preferably, each of the oral hygiene instruments 36 shown in FIG. 1 is included.

Each of the oral hygiene instruments, with the possible exception of the denta swab 56, includes an attachment shroud 60. (Unlike the other instruments, the denta swab 56 is also generally solid and does not provide suction therethrough). The attachment shroud 60 is used to connect the oral hygiene instrument 36 to the universal handle 20. (When not provided with an attachment shroud 60, the base 56a of the denta swab 56 will be configured to nest within the adapter end 32). As will be described in additional detail below, the attachment shroud 60 strengthens the attachment of the oral hygiene instruments 36 to the handle 20. Additionally, the attachment shroud 60 is configured to minimize internal and external contamination of adapter end 32 of the handle 20, to thereby inhibit the transfer of bacteria and viruses between a patient and the health care professional utilizing the system.

While each of the oral hygiene instruments-may be used exclusively for suction, they may also be configured for use in lavage. For example in FIG. 1, the toothbrush 40 has a liquid supply tube 64 which is connected to a passage (not shown) inside the toothbrush. A lavage solution from the lavage supply source 28 can be passed through the liquid supply tube 64 and the passage to provide lavage solution into the patient's mouth. A Luer fitting 68 is disposed on the end of the liquid supply tube 64 to facilitate attachment of the liquid supply tube to the lavage supply source 28. Of course, the liquid supply tube and the suction tube extending through the toothbrush could be formed as a single body, dual lumen design.

In use, the lavage supply source 28 is mounted in the universal handle 20, as indicated at 28a. The lavage supply source 28 is typically in the form of a vial made out of a flexible plastic, such as those which are commonly available in the medical products industry. Ideally, the lavage supply source 28 will hold approximately 20 ml of lavage liquid. The lavage liquid may be water, or may be a solution containing a antiseptic dentifrice.

The lavage supply source is attached to the universal handle 20 so that the user's fingers are disposed about the vial. By squeezing one or more fingers inwardly toward the universal handle 20, the user collapses the lavage supply source 28 and forces lavage solution out of the vial. By controlling the amount of pressure applied to the lavage supply source, the user can control the rate and quantity of lavage solution which flows out of the lavage supply source 28 and into the patient's mouth.

In addition to manual control of the lavage solution, the suction provided through the universal handle 20 is also controlled manually. Preferably, the universal handle 20 is provided with a sliding gate valve 70, such as that disclosed in U.S. Pat. No. 3,645,497. The sliding gate valve 70 enables the user to slide the valve open and closed with a simple move of the user's thumb. Thus, the user is able to control suction being provided through the universal handle 20 and oral hygiene instrument.

Also shown in FIG. 1 is a tube clip 74 which is disposed on the universal housing 20 to extend below the position of the lavage supply source 28. The tube clip 74 is configured to engage the suction tube 24, to thereby enable the universal handle 20 to hang on the suction tube. Those familiar with hospitals and the like will appreciate that most have a suction source which may be accessed adjacent each patient. Thus, the suction tube 24 will typically be attached to the wall and extend downwardly therefrom. The tube clip 74 enables attachment of the universal handle 20 to the suction tube to provide a convenient holding position, both while the user prepares for cleaning a patient's mouth and when the universal handle is not in use.

Figure 1A:
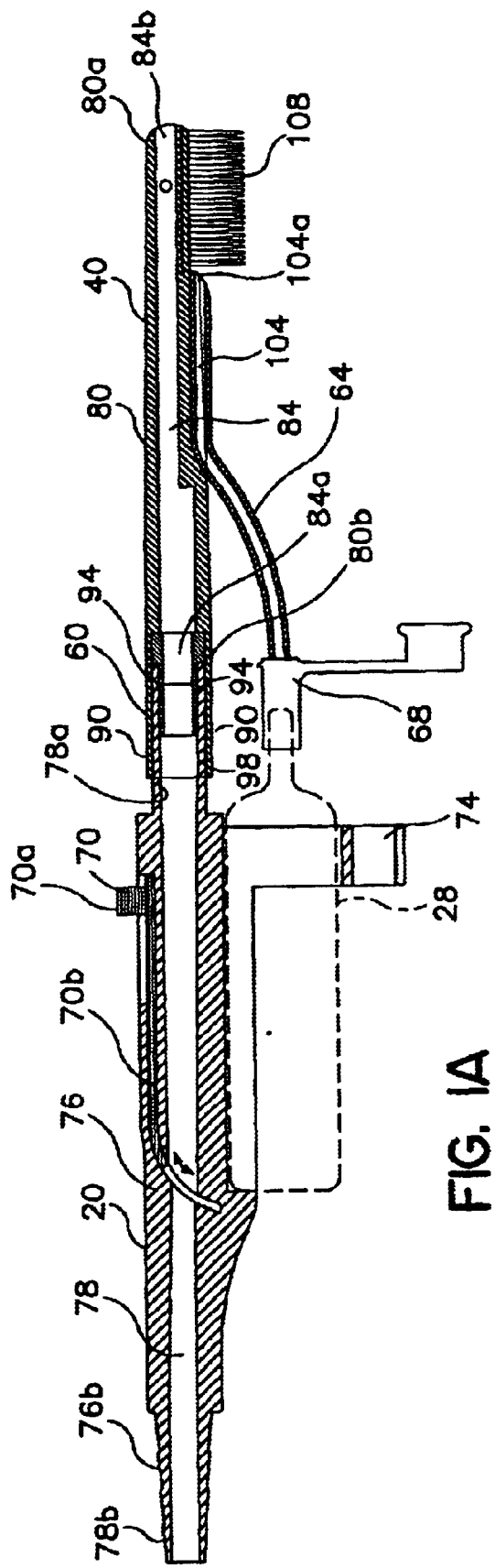
FIG. 1A shows a side cross-sectional view of the universal handle and toothbrush attached thereto for cleaning a patient's mouth.

Turning now to FIG. 1A, there is shown a cross-sectional view of the universal handle 20 and a toothbrush 40 connected thereto in accordance with the principles of the present invention. The universal handle 20 is formed by a two piece body 76 which defines a fluid flow passage 78. The fluid flow passage 78 has a proximal end 78a adjacent the adapter end 32, and a distal end 78b. About the distal end 78b of the passage 78, the body 76 has a distal portion 76b which is tapered and barbed so as to receive a suction tube (not shown)

The toothbrush 40 is also formed by an elongate body 80, which has a proximal end 80a and a distal end 80b. The body 80 defines a fluid flow passage 84 extending axially therethrough, such that the fluid flow passage 84 also has a proximal end 84a and a distal end 84b, both of which are open. Thus, a continuous passage is formed through the toothbrush 40 and universal handle 20 when the two are attached to one another.

In accordance with one aspect of the present invention, the toothbrush body 80 is provided with an attachment shroud 60 at the distal end 80b thereof. The attachment shroud 60 is formed by a generally annular outer wall 90, and a generally annular inner wall 94. The adapter end 32 of the universal housing 20 is also formed from a generally annular wall 98. The outer wall 90 and the inner flange of the annular inner wall 94 are configured to engage the annular wall 90 of the adapter end 32, so as to sandwich the generally annular wall 90 of the adapter end 32 between them. Such an engagement serves two important functions. First, because the outer wall 90 and the inner wall 94 are disposed on opposing sides of the generally annular wall 98, the attachment of the toothbrush 40 to the adapter end 32 is sufficiently strong to hold the toothbrush in position while it is being used. While the toothbrush 40 may be easily slid onto and removed from the adapter end 32 by applying a small amount of torque upon the toothbrush in the axial direction, significant transverse force is necessary to separate the attachment shroud 60 from the adapter end of the universal housing. Second, the outer wall 90 and the inner wall 94 of the shroud attachment 60 cover or shield each side of the adapter end 32 to minimize contamination of the adapter end. The outer wall 90 prevents external contamination by covering the outer surface of the generally annular wall 98, while the inner wall 94 shields the inner surface of the generally annular wall from contamination. While bacteria and viruses will commonly be in the distal portions of the flow passage 78, the shroud attachment 60 on the toothbrush 40 helps to minimize contamination of the adapter end 32 of the universal housing 20. This, in turn, minimizes the risk that health care professionals using the universal handle 20 will come into direct contact with the pathogens.

As will be apparent from FIG. 1A, the various components are designed for simplicity of manufacture and use. Each aspect of the oral care system 10 is manual and easy to use. For example, the nurse, etc., cleaning the patient's mouth may desire to first rinse away any food particles and dried saliva. Thus, he or she need merely squeeze on the vial which forms the lavage supply source 28. Squeezing vial forces lavage solution (water or some other desired solution) out through the luer fitting 68 and the liquid supply tube 64. The solution is then forced down a secondary flow passage 104 and out a proximal opening 104a near bristles 108 attached to the proximal end 80a of the toothbrush body 80. Because control of the lavage solution flow is controlled manually by squeezing the lavage solution supply source 28, the user can regulate the amount and rate of solution supplied simply by regulating the amount of pressure placed on the lavage solution supply source by the user's hand.

Control over the suction supplied through the toothbrush body 80 is simple. The gate valve 70 is disposed in the body 76 of the universal handle 20 at the joinder of the two pieces of the body. The gate valve 70 is formed by a slidable lug 70a which extends slightly above the body 76 of the universal handle 20, and a slidable gate 70b which is attached to the slidable lug and which selectively intersects the fluid flow passage 78 in the body of the universal handle. In the position shown in FIG. 1A, the gate bisects the passage 78 and prevents suction from being developed proximally from the gate. Sliding the slidable lug 70*a* forward, however, slides the gate upwardly and forwardly and thereby allows suction throughout the fluid flow passage 78 in the universal handle 20, and in the fluid flow passage 84 in the toothbrush body 80. The extent to which the gate 70*b* is slid controls the extent to which it obstructs the fluid flow passage 78, and thus regulates the amount of suction delivered at the proximal end 80*a* of the toothbrush body 80.

By controlling the injection of lavage solution from the lavage solution supply source 28, and by controlling the movement of the gate valve 70, the user is provided with complete control over both suction and lavage. Additionally, because of the manner in which the universal handle 20 is configured, complete control over suction and lavage may be provided by the thumb and forefinger of the user. The thumb is placed on the slidable lug 70*a* to control the gate valve 70, while the forefinger can easily control flow of lavage solution from the lavage supply source 28.

While FIG. 1A shows only the universal handle 20 and the toothbrush 40, those skilled in the art will appreciate that any of the other oral hygiene instruments 36 shown in FIG. 1 could be provided with both suction and fluid supply passages. Attaching or removing each of the devices takes less than one second, thereby enabling the user to select the desired oral hygiene instrument, or to interchange them during use. If food particles are stuck between the cheek and gum of the patient, the user need merely disconnect the toothbrush 40, and attach either the oropharangeal catheter 44 or the yankauer catheter 48 to the adapter end 32 of the universal handle 20. If the soft tissue of the patient's mouth needs to be cleaned, the catheter 44 or 48 can be replaced by either the suction swab 52 or the denta swab 56.

Thus, within a very short time the health care professional can thoroughly clean the patient's mouth. Periodic thorough cleanings will promote better oral hygiene and prevent sores and other infections in the patient's mouth.

Figure 2:
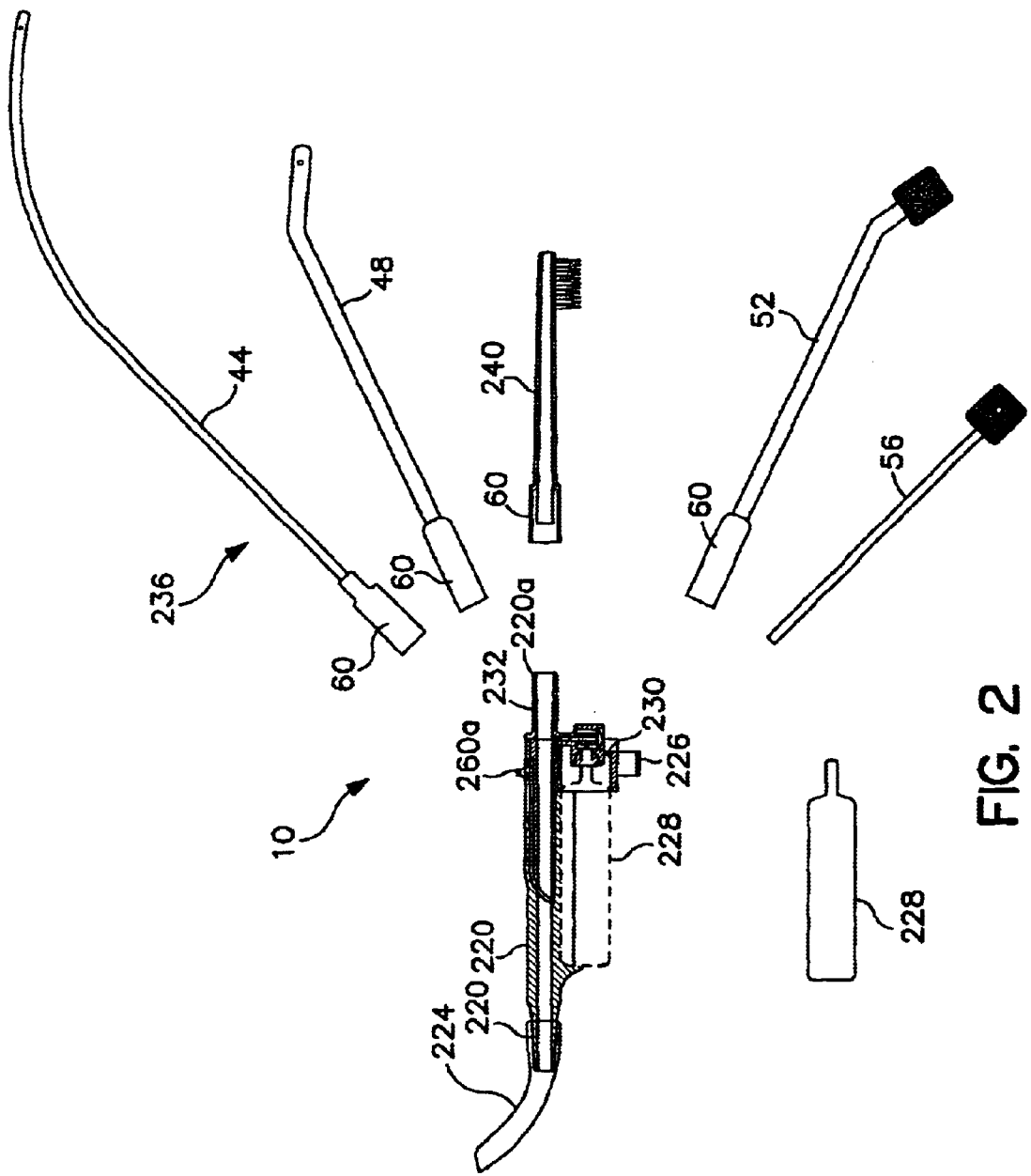
FIG. 2 shows an alternate embodiment of a universal handle, a lavage source, and a plurality of oral hygiene instruments made in accordance with the principles of the present invention.

Turning now to FIG. 2, there is shown an alternate embodiment of an oral care system, generally indicated at 210, made in accordance with the principles of the present invention. The oral care system 210 includes a universal handle 220 (shown in cross-section) which is similar in many respects to the universal handle 20 shown in FIGS. 1 and 1A. The universal handle 220 has a lavage supply source 228, typically in the form of a flexible plastic bottle, partially nested therein. The open end (not shown) of the lavage supply source 228 is disposed in a lavage control housing 230 which is formed by a portion of the universal handle 220. The lavage control housing 230 is discussed in detail with respects to FIGS. 3A through 3C. A tube clip 226 is also shown for attachment to a suction tube.

The universal handle 220 includes an adapter end 232, similar to that shown in FIG. 1, which is disposed at the handle's proximal end 220*a*. The distal end 220*b* of the universal handle 220 is configured to receive a suction tube 224. Such a suction tube 224 would typically be configured for connection to a wall suction outlet (not shown) such as those which are commonly used in hospitals and nursing homes. However, a portable suction device (not shown) could also be used.

The adapter end 232 formed at the proximal end 220*a* of the universal handle 220 is configured to engage any of a plurality of instruments, generally indicated at 236. Thus, FIG. 2 shows the oropharangeal catheter 44, the yankauer catheter 48, the suction swab 52 and the denta swab 56 which were shown in FIG. 1. FIG. 2 also shows a toothbrush 240 (shown in cross-section) which is attachable to the adapter end 232 of the universal handle 220, but which is configured differently than the toothbrush 40 shown in FIG. 1. Specifically, the toothbrush 240 shown in FIG. 2 does not utilize a liquid supply tube 64 or a secondary flow passage 104 (FIG. 1A). Rather, all of the oral hygiene instruments shown in FIG. 2 are configured with only a single fluid flow passage. Thus, as will be explained with additional detail with respect to FIGS. 2A through 3C, the same fluid flow passage is used both for lavage and suction. The lavage control housing 230 is configured to prevent suction through the instruments from withdrawing lavage solution from the lavage supply source 228.

The oropharangeal catheter 44, the yankauer catheter 48, the suction swab 52, and the toothbrush 240 are all provided with a shroud attachment 60 similar to that discussed above with respect to FIGS. 1 and 1A. The shroud attachment 60 helps to hold the oral hygiene instruments on the universal handle 220, and helps to reduce the risk of bacteria and other microbes being passed between patients and health care workers. Because the adapter end 232 is shielded by the attachment shroud 60, the user need not worry if he or she contacts the adapter end, as the contamination is disposed in the internal portion of the universal handle 220.

Also shown in FIG. 2 is the slidable lug 260*a* of a gate valve (FIG. 2A) which is disposed in the universal handle 220. Sliding the slidable lug 260*a* controls the amount of suction applied through the universal handle 220, and through the oral hygiene instrument 36 attached to the universal handle.

Figure 2A:
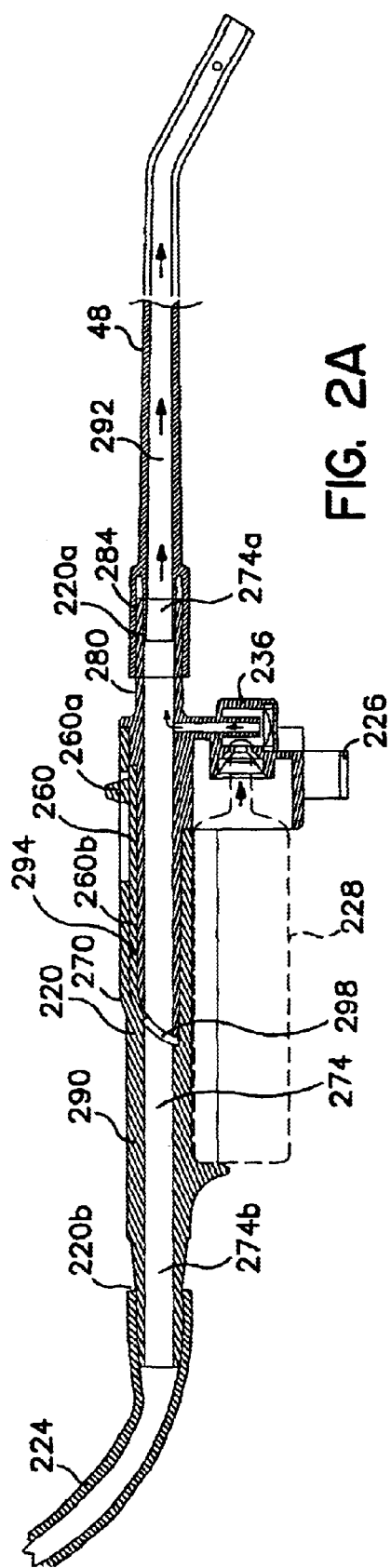
FIG. 2A shows a cross-sectional view of the universal handle shown in FIG. 2, with a yankauer catheter attached thereto for cleaning the mouth of a patient.

Turning now to FIG. 2A, there is shown a side, cross-sectional view of the universal handle 220 and a yankauer catheter 48. The universal handle 220 includes a body 270 which defines an elongate fluid flow passage 274 which extends axially through the handle. The body 270 of the universal handle 220 is formed from two housing portions. A proximal housing portion 280 includes the lavage control housing 230, and a sidewall 284 which defines a proximal portion 274*a* of the fluid flow passage 274 and which also forms the adapter end 232.

A distal housing portion 290 of the universal handle 220 forms the distal portion 274*b* of the fluid flow passage 274. The distal housing portion 290 also includes a void 294 which is configured to receive the proximal housing portion 280. When the proximal housing portion 280 is nested in the void 294, a small channel 298 is formed between the proximal portion and distal portion 290. The channel is configured to receive the slidable gate 260*b* of the gate valve 260. The gate valve 260 is slidable to selectively terminate or control fluid flow through the fluid flow passage 274 in the same manner as discussed with respect to FIGS. 1 and 1A and will not be discussed in additional detail.

Also shown in additional detail in FIG. 2A is the lavage control housing 230. The lavage control housing 230 is configured both to receive the lavage supply source 228 (FIG. 2) and to control fluid flow out of the lavage supply source 228 when the gate valve 260 is moved into position to provide suction through the fluid flow passage 274.

When lavage solution is ejected from the lavage control housing 230 and the gate valve 260 is disposed in the closed position (as shown in FIG. 1A), the solution flows into the proximal portion 274*a* of the fluid flow passage 274 of the universal handle 220, and into the fluid flow passage 292 extending through the catheter 48. Thus, the lavage solution is passed to the patient's mouth where it can be used for cleaning. The gate valve 260 is then moved into the open position shown in FIG. 2A, and the lavage solution, food particles and saliva are withdrawn from the patient's mouth.

Once the patient's mouth has been cleaned, there will usually be several milliliters of solution in the lavage supply source 228. By opening the gate valve 260 and forcing the solution out of the lavage supply source 228, the solution is disposed of, and the fluid flow passage 274 of the universal handle 220 is rinsed to remove any food particles or saliva still contained therein.

While rinsing the fluid flow passage 274 of the universal handle 220 is advantageous, it is undesirable for the suction to continuously withdraw solution from the lavage supply source 228. To prevent continued withdrawal of the solution, the universal handle 220 includes the lavage control housing 230.

Figure 3A:
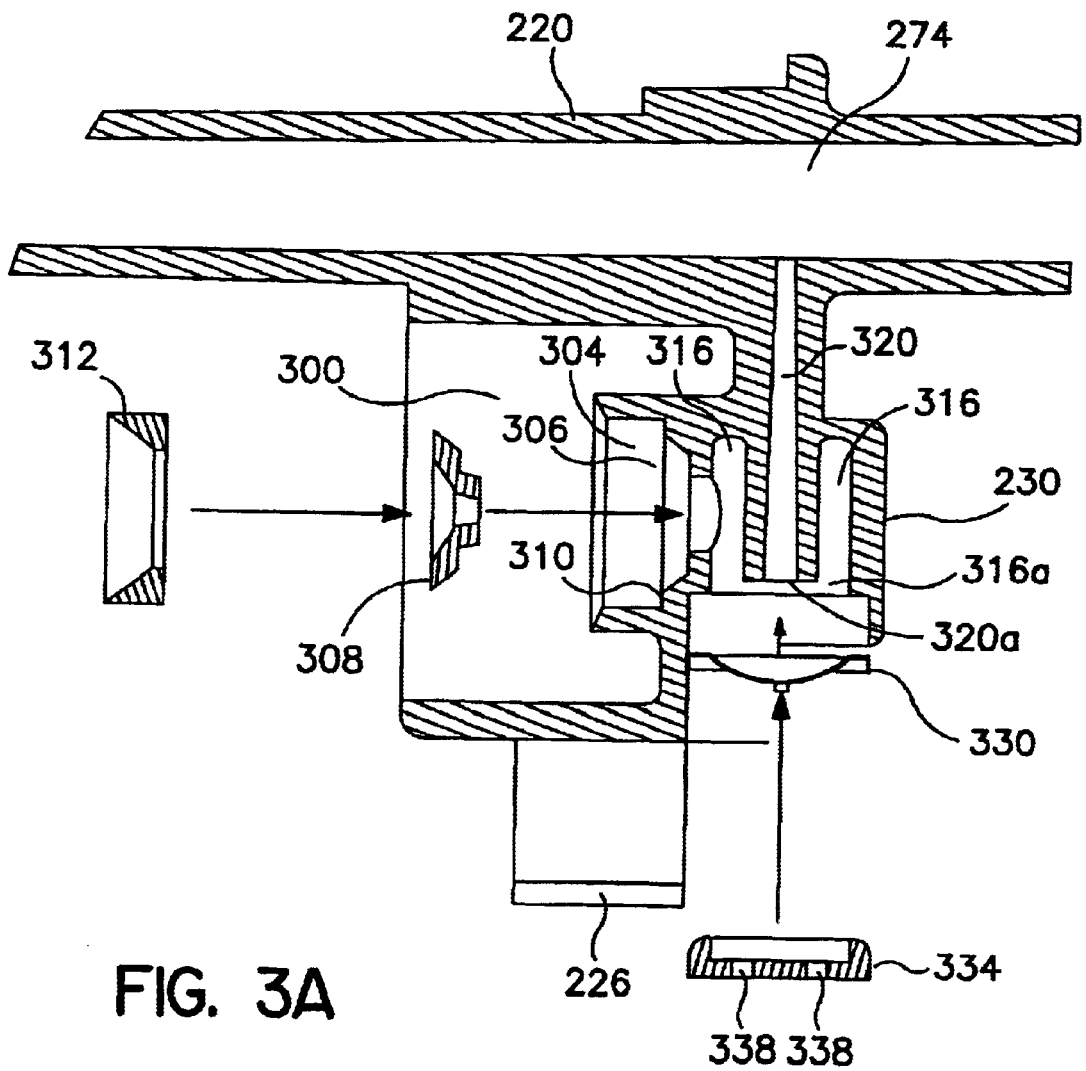
FIG. 3A shows a close-up, exploded view of the valve configuration of a lavage control housing used to control flow of the lavage.

A close-up, exploded view of the lavage-control housing 230 and its parts is shown in FIG. 3A, and assembled views of the lavage control housing with the valve in open and closed positions are shown in FIGS. 3B and 3C. The lavage control housing 230 includes a first, distal lavage receiving portion 300 which is configured for receiving the lavage supply source 228 (FIGS. 2 and 2A). The first, distal portion 300 includes a contoured void 304 which is defined by a first, sloped shoulder 306 configured for receiving a vial seal 308. The void 304 is also configured with a second, squared shoulder 310 which is configured to receive a vial seal retainer 312. As the name implies, the vial seal retainer 312 holds the vial seal 308 in place when the two are positioned in the void 304.

When the vial seal 308 and the vial seal retainer 312 are set in place, the lavage supply source 228 (FIG. 2) is able to nest snugly in the first, distal lavage receiving portion 300. The vial seal 308 engages the vial of the lavage supply source 228 about its opening, thereby preventing leaks when pressure is applied to the vial.

The lavage control housing 230 also includes a plurality of channels which are disposed in fluid communication with the void 304. A first lavage flow channel 316 is disposed in communication with the void 304 such that lavage solution flowing out of a lavage supply source nested in the void flows into the first lavage flow channel 316. In the embodiment shown in FIG. 3A, the first lavage flow channel 316 is generally annular.

The first lavage flow channel 316 is disposed in fluid communication with a second lavage flow channel 320. Preferably, the first and second lavage flow channels 316 and 320 are disposed in parallel with one another. Thus, the lavage flowing through the control housing must reverse direction before being released into the fluid flow passage 274 of the universal handle 220.

Disposed adjacent an end 316a of the first lavage flow channel 316, and adjacent a common end 320a of the second lavage flow channel 320 is a dome valve 330. The dome valve 330 is held in position adjacent the ends 316a and 320a of the first and second lavage flow channels 320 by a dome valve retainer 334. The dome valve retainer 334 includes at least one air passage 338 therethrough, the purpose of which will be discussed momentarily.

The dome valve 330 of FIGS. 3A through 3C is highly advantageous because it enables passive control over the flow of fluid out of the lavage supply source 228. By passive control, it is meant that the dome valve 330 will automatically terminate fluid flow into the fluid flow passage 274 to prevent suction from draining the lavage supply source 228, without any action on the part of the user, and without interfering with fluid flow in the event the user desires to supply solution simultaneously with suction.

The dome valve 330 is formed of a thin vane of resilient, impermeable material. When the pressure within the first and second lavage flow channels 316 and 320 is the same or greater than the pressure on the opposite side of dome valve 330 (i.e. ambient pressure outside the lavage control housing 230), the dome valve remains in an open position as shown in FIG. 3B. In such a position, the lavage solution passes through an opening 342 at the proximal end of the void 304, into the first lavage flow channel 316 and into second lavage flow channel 320 as indicated by the arrows. The lavage solution is then passed into the fluid flow passage 274 extending through the universal handle 220.

When suction is applied by opening the gate valve 260 (FIG. 2A), the pressures within the lavage control housing 230 change. First, the pressure in the first and second lavage flow channels 316 and 320 drops. Once the pressure inside the second lavage flow channels 316 and 320 falls sufficiently below the pressure on the opposite side of the dome valve 330, the dome valve inverts and covers the end 320a of the second lavage flow channel 320, thereby terminating fluid communication between the first lavage flow channel 316 and the second lavage flow channel 320. The pressure differential on opposing sides of the dome valve 330 which is necessary to cause the dome valve to invert and terminate fluid communication between the first lavage flow channel 316 and the second lavage flow channel 320 depends on the thickness of the dome valve and the material from which it is made. By routine experimentation, those skilled in the art will be able to obtain a dome valve 330 which inverts at nearly any desired pressure differential. The channels 338 in the dome valve retainer 334 are formed to place the dome valve 330 in fluid communication with air at ambient pressure.

When suction is applied in the fluid flow passage 274, a negative pressure in the second lavage flow channel 320 maintains the dome valve 330 in the closed position shown in FIG. 3C. With the dome valve 330 in such a position, the suction applied to the fluid flow passage 274 cannot withdraw the solution from the lavage supply source 228 (FIGS. 2 and 2A).

There are, however, times when the user will want lavage solution to flow into the fluid flow passage 274 when suction is being applied. For example, when the user is finished cleaning the patient's mouth, the inside of the handle 220 must be rinsed, and it is preferable to dispose of most of the lavage solution in the lavage supply source 228. This is accomplished by applying pressure to the lavage supply source 228 in the same manner as is done to supply lavage when the suction is not present. The pressure on the lavage supply source 228 forces the lavage solution into the first lavage flow channel 316 at a pressure higher than the ambient pressure on the opposite side of the dome valve. The higher pressure in the first lavage flow channel 316 moves the dome valve 330 back into the position shown in FIG. 3B, thereby allowing the lavage solution to flow through the lavage control housing 230. Thus, the user can flush the universal handle with solution to remove any food particles or saliva which may remain therein. After rinsing is completed, the universal handle 220 is attached to the suction tube by the tube clip 226 until it is needed again.

Turning now to FIG. 4A, there is shown a cross-sectional view of the toothbrush shown in FIG. 2. The toothbrush 240 includes an elongate fluid flow passage 350 which extends from a proximal opening 350a at the proximal end 240a of the toothbrush, to a distal opening 350b at a distal end 240b of the toothbrush. An attachment shroud 60 is formed at the distal end 240b of the toothbrush 240 to facilitate attachment to the adapter end 232 of the universal handle 220.

The fluid flow passage 350 of the toothbrush is substantially linear, so that food particles and liquids can be drawn into the distal end 240b of the toothbrush and provided with a straight flow path through the universal housing 220 (FIGS. 2 and 2A). Because the opening is at the distal tip of the toothbrush 240 is generally easier to form than many of the suction toothbrushes of the prior art. Additionally, the position of the opening makes it less likely that the soft tissue of the mouth will seal off the opening. To further reduce the risk of such a situation, a small suction relief port 360 is provided distally from the bristles 354. With such a configuration, the toothbrush 240 obtains the advantages sought by the prior art, but without the disadvantages.

When lavage is desired, the user need only squeeze the lavage supply source 228 and the lavage solution will flow through the fluid flow passage 350. Suction is then applied through the same passage to withdraw the lavage solution, as well as any food particles and saliva in the patient's mouth. Such a toothbrush 240 is much less expensive to produce than the configurations of the prior art, and facilitates low cost. The lower the cost for the overall oral care system 210, the more likely it is that each patient will be provided with appropriate oral hygiene.

Figure 4B:
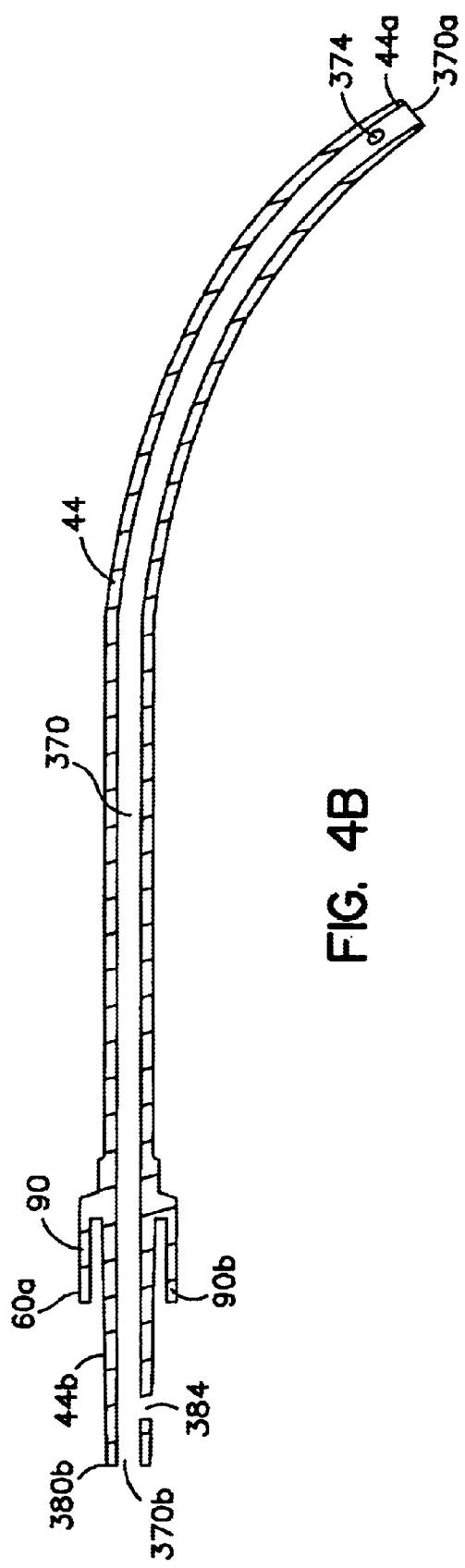
FIG. 4B shows a cross-sectional view of the oropharangeal catheter shown in FIG. 2 with a modification to the attachment shroud.

FIG. 4B shows a cross-sectional view of the oropharangeal catheter 44 shown in FIG. 2 with a modification to the attachment shroud 60a. The oropharangeal catheter 44 has an elongate fluid flow passage 370 which extends from a proximal opening 370a at the proximal end 44 of the catheter, to a distal opening 370b at a distal end 44b of the catheter. Disposed adjacent the proximal end 44a is a suction relief opening 374. The suction relief opening 374 assists in the withdrawal of liquids and food particles from the patient's mouth, and also minimizes the amount of direction suction which can be applied to the soft tissue of the mouth in the event that the proximal end 44a of the catheter 44 suctionally engages the tissue.

One significant difference shown in the oropharangeal catheter 44 is the configuration of the attachment shroud 60a. The attachment shroud 60a is formed by an outer wall 90 which is substantially the same as that described with respect of the prior embodiments. The inner wall 380, however, extends well beyond the distal end 90b of the outer wall 90. Preferably, the inner wall 380 is sufficiently long that the the inner wall will extend rearwardly of the juncture between the fluid flow passage 274 (FIGS. 2A through 3C) and the second lavage flow channel 320 when inserted into the universal handle 220 (FIGS. 2 and 2A). A small hole 384 is formed in the inner wall to enable lavage solution to flow into the oropharangeal catheter 44 from the lavage control housing 230. At the same time, the interior of the handle 220 is protected from contamination by materials suctioned out of the patient's mouth back to the distal end of the inner wall. If the inner wall were sufficiently long to extend back to the gate valve 260, contamination of the proximal portion of the fluid flow passage 274 of the universal handle 220 would be eliminated.

Turning now to FIG. 4C, there is shown a cross-sectional view of the suction swab 52 shown in FIG. 2. The suction swab 52 is preferably formed by using a yankauer catheter similar to that shown in FIG. 2A. The catheter body 390 defines a fluid flow passage 394 extending from and open proximal end 394a at the proximal end 390a of the catheter body, to a distal opening 394b at the distal end 390b of the catheter body. An attachment shroud 60 is also formed at the distal end 390b of the catheter body in the manner discussed with respect to FIG. 2A.

A resilient material 398 is attached adjacent the proximal end 390a of the catheter body 390. The resilient material enables the user scrub the tissue of the patient's mouth without damaging the tissue. While cotton can be used, a soft, plastic material, which does not mat when wet, is preferred.

When desired, lavage solution can be added to facilitate cleaning of the patient's mouth by simply squeezing the lavage supply source 228 in the manner described above. Once the liquid is no longer needed in the mouth, the user need merely slide the slidable lug 260a (FIG. 2A) of the gate valve 260 (FIG. 2A) forward, to thereby provide suction through the fluid flow passage 394. A relief opening 374 is also provided to ensure that complete suction is not accidentally achieved on the soft tissues of the patient's mouth.

Using these tools, health care professionals can quickly and thoroughly clean a patient's mouth. With food particles and bacteria removed, the patient is less likely to suffer from sores, halitosis and oral infections. At the same time, contact between the health care worker and the patient's saliva etc. are kept to a minimum, thereby decreasing safety concerns.

Thus there is disclosed an improved oral care system. Those skilled in the art will appreciate numerous modifications which can be made without departing from the scope and spirit of the present invention. The appended claims are intended to cover such modifications and their functional equivalents.

What is claimed is:

1. An oral care system comprising:
   a universal handle means having a body with a fluid flow passage formed therethrough, the body having a proximal end with an adapter with an interior and exterior, the adapter being configured for attachment to any of a plurality of oral hygiene instruments, and a distal end configured for attachment to a suction supply source, said universal handle means adapted to draw liquids and particles into and through said fluid flow passage when suction is applied to the proximal end of said body;
   a plurality of oral hygiene instruments, said instruments being configured for attachment to the proximal end of the universal housing, each of said plurality of oral hygiene instruments having at least one fluid flow passage extending therethrough and disposed so as to be in fluid communication with the fluid flow passage of the universal handle to facilitate suctioning of liquids and particles therethrough; and
   attachment means configured for connecting each of the plurality of instruments to the universal handle means, the attachment means comprising a shielding means extending so as to cover the interior and exterior of the adapter and thereby minimize contamination of the adapter.

2. The oral care system of claim 1, wherein the adapter comprises a generally annular wall, and wherein the attachment means comprises a generally annular inner wall and a generally annular outer wall spaced apart from one another sufficiently to receive the generally annular wall of the adapter, and thereby sandwich the generally annular wall of the adapter between the inner wall and the outer wall and thereby shield the interior and exterior of the adapter from contamination.

3. The oral care system of claim 2, wherein each of the plurality of oral hygiene instruments has a proximal end and a distal end, and wherein the attachment means is integrally formed at the distal end of each of the plurality of oral hygiene instruments.

4. The oral care system of claim 1, wherein the oral care system further comprises lavage means attached to the universal handle for supplying a lavage liquid through the fluid flow passage of each of the plurality of oral hygiene instruments.

5. The oral care system of claim 4, wherein the lavage means comprises a disposable lavage supply source attachable to the universal handle so as to be carried by the universal handle during use.

6. The oral care system of claim 5, wherein the lavage supply source nests at least partially within the handle.

7. The oral care system of claim 5, wherein the lavage supply source is configured to inject lavage liquid through the fluid flow passage of the plurality of oral hygiene instruments when the user squeezes the lavage supply source.

8. The oral care system of claim 5, wherein the universal handle comprises a lavage control housing configured for engaging the lavage supply source so as to receive lavage liquid from the lavage supply source when pressure is applied to the lavage supply source, and having at least one lavage flow channel, and a valve means disposed in communication with the at least one lavage flow channel for selectively terminating flow through the lavage flow channel.

9. The oral care system of claim 6, wherein the valve means is configured for responding to suction within the lavage flow channel, such that application of suction to the lavage flow channel downstream from the valve means causes said valve means to automatically terminate fluid through the at least one lavage flow channel.

10. The oral care system of claim 9, wherein the valve means comprises a dome valve.

11. The oral care system of claim 10, wherein the at least one lavage flow channel comprises a first lavage control channel disposed in fluid communication with the lavage supply source when the lavage supply source engages the lavage control housing, and a second lavage flow channel disposed in fluid communication with the first lavage flow channel and with the fluid flow passage of one of the plurality of instruments when said one of said plurality of instruments is attached to the universal handle, and wherein the dome valve is disposed to terminate fluid flow between the first lavage channel and the second lavage flow channel when a negative pressure is present in the at least one lavage flow channels.

12. The oral care system of claim 11, wherein the second lavage flow channel extends from the valve means to an opening in the fluid flow passage of the handle.

13. The oral care system of claim 4, wherein each of the plurality of oral hygiene instruments has a single fluid flow passage configured for lavage and suction, and wherein the universal handle is configured for directing lavage and suction through said single fluid flow passage.

14. An oral care system comprising:
a universal handle means having a body with a fluid flow passage formed therethrough, the body having a proximal end with an adapter with an interior and exterior, the adapter being configured for attachment to any of a plurality of oral hygiene instruments, and a distal end configured for attachment to a suction supply source;
a plurality of oral hygiene instruments, said instruments being configured for attachment to the proximal end of the universal housing, each of said plurality of oral hygiene instruments having at least one fluid flow passage extending therethrough and disposed so as to be in fluid communication with the fluid flow passage of the universal handle to facilitate suctioning of liquids and particles therethrough, wherein the plurality of oral hygiene instruments includes a toothbrush and a oropharangeal catheter; and
attachment means configured for connecting each of the plurality of instruments to the universal handle means, the attachment means comprising a shielding means extending so as to cover the interior and exterior of the adapter and thereby minimize contamination of the adapter.

15. An oral care system comprising:
a universal handle means having a body with a fluid flow passage formed therethrough, the body having a proximal end with an adapter with an interior and exterior, the adapter being configured for attachment to any of a plurality of oral hygiene instruments, and a distal end configured for attachment to a suction supply source;
a plurality of oral hygiene instruments, said instruments being configured for attachment to the proximal end of the universal housing, each of said plurality of oral hygiene instruments having at least one fluid flow passage extending therethrough and disposed so as to be in fluid communication with the fluid flow passage of the universal handle to facilitate suctioning of liquids and particles therethrough, wherein the plurality of oral hygiene instruments includes a toothbrush and a suction swab; and
attachment means configured for connecting each of the plurality of instruments to the universal handle means, the attachment means comprising a shielding means extending so as to cover the interior and exterior of the adapter and thereby minimize contamination of the adapter.

16. An oral care system for cleaning a patient's mouth, the oral care system comprising:
a universal handle means having a body with a fluid flow passage formed therethrough, the body having a proximal end with an adapter with an interior and exterior, the adapter being configured for attachment to any of a plurality of oral hygiene instruments, and a distal end configured for attachment to a suction tube;
a plurality of oral hygiene instruments, said instruments being configured for attachment to the proximal end of the universal housing, each of said plurality of oral hygiene instruments having at least one fluid flow passage extending therethrough and disposed so as to be in fluid communication with the fluid flow passage of the universal handle to facilitate suctioning of liquids and particles therethrough; and
lavage means attachable to the universal handle so as to be carried by the universal handle, the lavage means including a disposable lavage supply source for injecting lavage liquid through the at least one fluid flow passage of at least one of the plurality of oral hygiene instruments, wherein the oral care system is configured for allowing lavage to be injected through the at least one fluid flow passage of at least one of the plurality of oral hygiene instruments at the same time as suction is applied to the proximal end of the body of the universal housing means.

17. The oral care system of claim 16, wherein the universal handle further comprises a lavage control housing for receiving the lavage means and for selectively controlling flow of lavage liquid out of the lavage supply source.

18. The oral care system of claim 17, wherein the lavage control housing further comprises at least one lavage flow channel for conveying lavage liquid from the lavage supply source to the at least one fluid flow passage of one of the plurality of oral hygiene instruments, and valve means for selectively terminating flow of lavage through the at least one lavage flow channel.

19. The oral care system of claim 18, wherein the at least one lavage flow channel comprises a first lavage flow channel and a second lavage flow channel, and wherein the valve means is disposed between the first and second lavage flow channels.

20. The oral care system of claim 19, wherein the second lavage flow channel has an opening leading into the fluid flow channel of the universal handle.

21. The oral care system of claim 19, wherein the first and second flow channels are disposed coaxially.

22. The oral care system of claim 19, wherein the valve means comprises a dome adjacent the first and second lavage flow channels, the dome valve having a first, open position, wherein the dome valve allows flow of lavage liquid from the first lavage flow channel to the second lavage flow channel, and a second, closed position wherein the dome valve prevents flow of lavage liquid from the first lavage flow channel to the second lavage flow channel.

23. The oral care system of claim 22, wherein the dome valve is pressure sensitive such that the creation of a negative pressure within the first lavage flow channel or the second lavage flow channel moves the dome valve from the first, open position to the second, closed position.

24. The oral care system of claim 23 further comprising a suction means for creating negative pressure within the fluid flow channel of the universal handle and wherein the second lavage flow channel is disposed in fluid communication with the fluid flow passage of the universal handle such that the generation of a negative pressure within the fluid flow passage of the universal handle creates negative pressure within the second lavage flow channel, thereby closing the dome valve and terminating fluid flow therethrough while suction is applied through the fluid flow passage of the universal handle.

25. The oral care system of claim 22, wherein applying pressure to the lavage supply source to eject lavage liquid therefrom while the dome valve is in the second, closed position forces lavage liquid through the first lavage flow channel and moves the dome valve into the first, open position.

26. The oral care system of claim 16, wherein each of the plurality of instruments includes an attachment shroud for connecting the instrument to the adapter of the universal handle so as to shield the interior and exterior of the adapter from contamination.

27. The oral care system of claim 26, further comprising at least one oral hygiene instrument configured for attachment to the universal handle, said hygiene instrument lacking an attachment shroud.

28. The oral care system of claim 27, wherein the at least one oral hygiene instrument being characterized by a generally solid shaft, thereby preventing the application of suction or lavage through the at least one oral hygiene instrument.

29. An oral care system comprising:
a universal handle means having a body with a fluid flow passage formed therethrough, the body having a proximal end with an adapter having an interior and exterior, the adapter being configured for attachment to any of a plurality of oral hygiene instruments, and a distal end configured for attachment to a suction tube;
a plurality of oral hygiene instruments, said instruments being configured for attachment to the proximal end of the universal housing, said plurality of oral hygiene instruments having at least one fluid flow passage extending therethrough and disposed so as to be in fluid communication with the fluid flow passage of the universal handle to facilitate suctioning of liquids and particles therethrough, at least one of the plurality of oral hygiene instruments including attachment means for connecting the at least one oral hygiene instrument to the universal means, the attachment means comprising a shielding means for covering the interior and exterior of the adapter to thereby minimize contamination of the adapter; and
lavage means attachable to the universal handle so as to be carried by the universal handle, the lavage means including a disposable lavage supply source for injecting lavage liquid through the at least one fluid flow passage of at least one of the plurality of oral hygiene instruments, wherein the oral care system is configured for allowing lavage to be injected through the at least one fluid flow passage of at least one of the plurality of oral hygiene instruments at the same time as suction is applied to the proximal end of the body of the universal housing means.

* * * * *